United States Patent

Bolz et al.

[11] Patent Number: 5,080,668
[45] Date of Patent: Jan. 14, 1992

[54] CARDIAC VALVE PROSTHESIS

[75] Inventors: Armin Bolz; Max Schaldach, both of Erlangen, Fed. Rep. of Germany

[73] Assignee: Biotronik Mess- und Therapiegeräte GmbH & Co. KG Ingenieurbüro Berlin, Berlin, Fed. Rep. of Germany

[21] Appl. No.: 442,790

[22] Filed: Nov. 29, 1989

[30] Foreign Application Priority Data

Nov. 29, 1988 [DE] Fed. Rep. of Germany ... 8815082[U]

[51] Int. Cl.$^5$ .................................................. A61F 2/24
[52] U.S. Cl. ............................................................ 623/2
[58] Field of Search .................................................. 623/2

[56] References Cited

U.S. PATENT DOCUMENTS

| | | | |
|---|---|---|---|
| 3,969,130 | 7/1976 | Bokros | 623/2 |
| 4,357,715 | 11/1982 | Klawitter | 137/527.8 |
| 4,674,434 | 6/1987 | Ishihara | 118/50.1 |
| 4,719,123 | 1/1988 | Haku et al. | 437/101 |
| 4,761,302 | 8/1988 | Weil | 427/39 |
| 4,863,467 | 9/1989 | Bokros | 623/2 |

FOREIGN PATENT DOCUMENTS

| | | | |
|---|---|---|---|
| 0232955 | 1/1987 | European Pat. Off. | |
| 0300512 | 1/1989 | European Pat. Off. | 623/2 |
| 1304810 | 4/1987 | U.S.S.R. | 623/2 |

OTHER PUBLICATIONS

Bolz, A.; New Coating Materials for Artificial Heart Valves; 1989; pp. 0164–0166.
Bolz, A. and M. Schaldach; Amorphous Semiconducting Coatings for the Improvement of Haemocompatibility; 1988; 6 pages.

*Primary Examiner*—Randy C. Shay
*Attorney, Agent, or Firm*—Spencer & Frank

[57] ABSTRACT

A cardiac valve prosthesis includes a rotatably mounted, disc-shaped valve flap which is provided with two outwardly oriented, convex attachments disposed opposite one another at the points of intersection of a secant with the edge of the disc. The valve also includes an annular body having on its interior wall first recesses for receiving the convex attachments to thus form a bearing socket for the valve flap. At its interior wall, the annular body is provided with second recesses which communicate with the first recesses to form a passage for the convex attachments during insertion thereof into the first recesses.

9 Claims, 3 Drawing Sheets

CARDIAC VALVE PROSTHESIS

CROSS REFERENCE TO RELATED APPLICATION

This application contains subject matter related to U.S. patent application Ser. No. 07/442,789, entitled SURGICAL IMPLANT HAVING A SEMICONDUCTIVE SURFACE (inventors: Armin Bolz and Max Schaldach), filed Nov. 29, 1989, which is a counterpart of Federal Republic of Germany Application No. G 88 15 083.6 filed Nov. 29, 1988.

This application claims the priority of Federal Republic of Germany Application No. G 88 15 082.8 filed Nov. 29, 1988, which is incorporated herein by reference.

BACKGROUND OF THE INVENTION

The present invention relates to a cardiac valve prosthesis composed of a rotatably mounted, disc-shaped valve flap and an annular body. The flap includes two outwardly oriented spherical cap-shaped convex attachments which face one another at the points of intersection of a secant of the valve flap with an edge thereof. The annular body includes an interior wall having recesses conforming to the convex attachments and for providing a seat for the valve flap.

Artificial cardiac valves of the above type involve the problem of maintaining the annular body supporting the valve flap as undeformed as possible during insertion of the valve flap so that it will not be permanently deformed and its surface coatings will not be damaged.

SUMMARY OF THE INVENTION

It is an object of the present invention to provide an improved cardiac valve prosthesis of the above-mentioned type which makes it possible to install the valve flap without deforming the annular body.

This object and others to become apparent as the specification progresses, are accomplished by the invention, according to which, briefly stated, the cardiac valve prosthesis has a rotatably mounted, disc-shaped valve flap which includes two outwardly oriented convex attachments at points of intersection of a secant of the valve flap with an edge thereof and an annular body including an interior wall having first recesses for receiving the convex attachments and for providing a bearing for the valve flap which is thus rotatable about an axis coinciding with the secant. The interior wall has second recesses communicating with the first recesses and forming a passage for the convex attachments during insertion of the valve flap into the first recesses when the valve flap is in an orientation which is beyond a fully open or a fully closed position thereof. The second recesses extend toward an exterior edge of the annular body.

The invention is based on the earlier recognition that if the annular body is provided with a groove in such a manner that the valve flap can be inserted into its seat exclusively in a position which it cannot assume hydrodynamically in the implanted state, then a deformation of the outer annular body is prevented and further, it is ensured that the valve flap cannot become disconnected from the bearing (bearing socket) in the operating state. Advantageously, by providing the interior wall of the annular body of the cardiac valve prosthesis with the above-defined second recesses which form a passage for the convex attachments to the upper and/or lower edge of the ring in such a position of the valve flap which is beyond a position which the flap is able to assume hydrodynamically, the safety of the patient is ensured without making installation more expensive.

According to a further feature of the invention, the convex attachments are able to pass through the passage when the valve flap is in an angular position which, based on an operating position, is disposed beyond the open or closed position defined by a first and second stop, respectively. In this way it is ensured that the angular position for insertion is not attained again in the implanted state. The first stop for the valve flap in its open position is preferably disposed behind the valve flap support when seen in the direction of flow and the second stop for the closed position of the valve flap is formed by an edge provided at the interior wall of the annular body. Both stops preferably have a barb-shaped cross section.

According to a further feature of the invention, the annular body is provided with a ledge disposed tangentially along the interior wall in a region between the two seats (valve supports) so as to limit flap movement in the direction beyond the closed position.

According to yet another advantageous feature of the invention, a semiconductive material is used as the coating for the implant for preventing the flow of electron currents which would enhance fibrin activation. To accomplish this, the surface layer may be extremely thin. The appropriate coatings can be produced cost-effectively by PVD (plasma vapor deposition) or CVD (chemical vapor deposition) methods. In this connection, the production of amorphous SiC according to the plasma assisted CVD method is particularly favorable. In this way, layers of a very low electrical state density can be produced.

The semiconductive coating is composed either of an amorphous or a microcrystalline material. The peak-to-valley height (roughness) of the surface is less than 0.1 $\mu$m. In this way, the agglomeration and destruction of corpuscular components of the blood and the activation of the coagulation system connected therewith are prevented. The solution is based on the concept that at the energy level of the electronic protein states in blood the state density of the coating is low. Thus, thrombogenic charge exchanges between coagulation-specific proteins and the implant surface are prevented.

Preferably, amorphous silicon carbide (a-SiC:H), a precipitation product of a mixture including silane ($SiH_4$) and/or methane ($CH_4$) is employed for the antithrombogenic coating. Silicon oxide (a-SiO:H) can advantageously be used as well.

In particular, the coating is made as free of pores as possible. This also increases its stability. Instead of silicon carbide, silicon nitride (a-SiN:H) can also be employed which, in this respect, has the same surface characteristics.

DESCRIPTION OF THE PREFERRED EMBODIMENT

Figure 1:
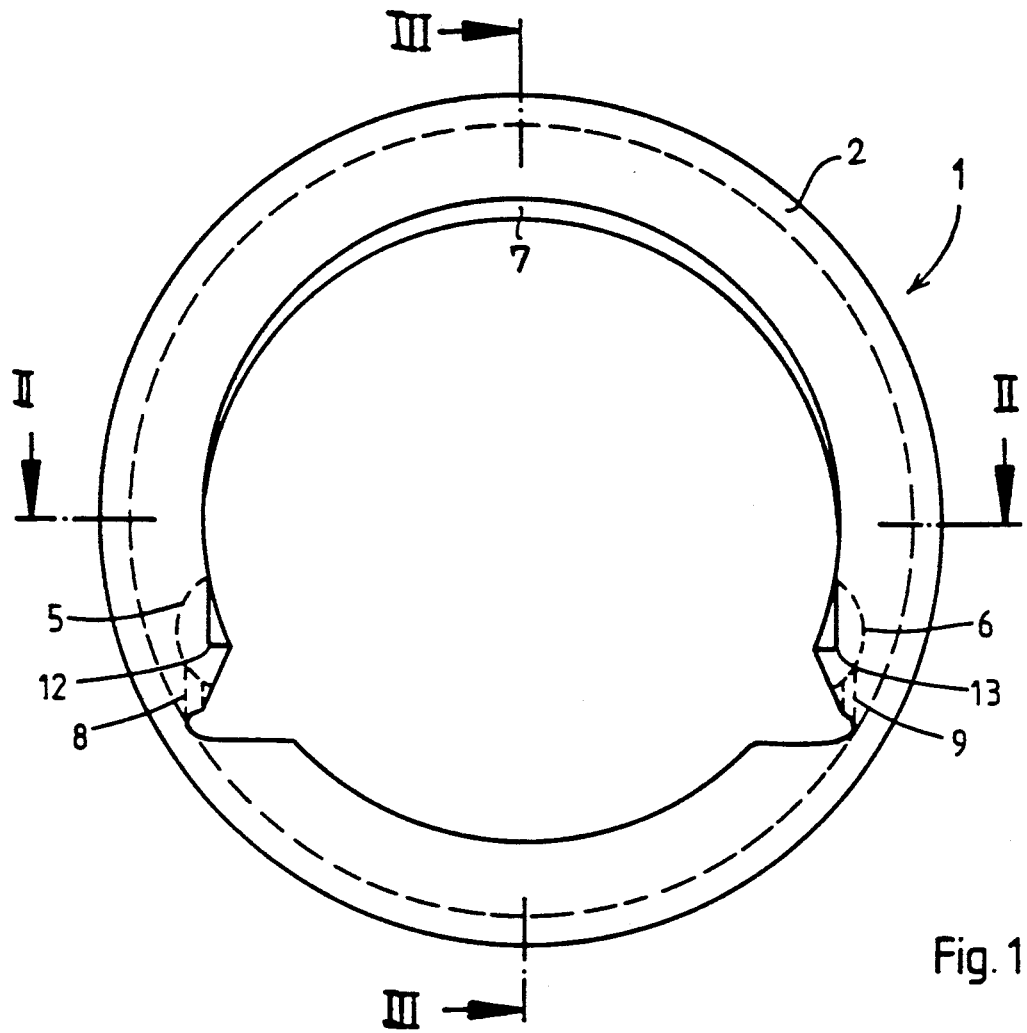
FIG. 1 is a plan view of the annular body of the cardiac valve prosthesis according to a preferred embodiment of the invention.
Figure 2:
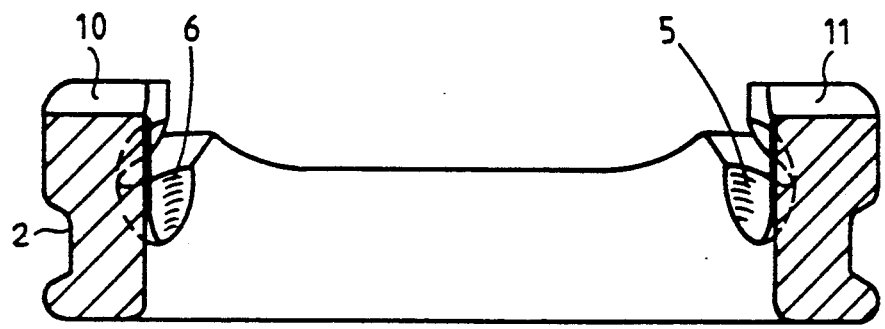
FIG. 2 is a sectional view along the line II—II of FIG. 1.

Of the preferred embodiment of the cardiac valve prosthesis according to the invention, only the annular body 1 is shown in FIG. 1; the valve body (flap) itself has been omitted for reasons of clarity. The annular body 1 is provided with a circumferential groove 2 for fastening the cardiac valve prosthesis by means of a force fit in a fissure of the live tissue. The valve flap 3 shown in the open position in FIG. 3b and in the closed position in FIG. 3a has two spherical attachments 4 (only one is visible) which are snapped in place into respective recesses (bearing sockets) 5 and 6. During operation the ball members 4 journal in the respective socket 5, 6 and thus form a rotary bearing therewith. The spherical attachments 4 form opposite ends of an axis of rotation for the valve flap 3. The axis of rotation corresponds to a secant of a circular disc filling the interior of the annular body 1. In this way, the forces acting on the larger portion of the circular disc partitioned by the secant predominate so that the valve flap 3 is opened or closed by the flowing blood. In the closed position, the valve flap 3 lies on an abutment ledge 7 which is provided in the interior wall of the annular body 1 and which extends parallel to the periphery thereof. The abutment ledge 7 preferably extends in that body region between the recesses 5 and 6 which is further from the rotation axis than the other, opposite region between the recesses 5 and 6.

The interior surface of the annular ring 1 has an inwardly extending abutment ledge 7 shaped with a generally crescent configuration and the inner diameter of the annular ring 1 widens in the direction of flap valve 3 under the abutment ledge 7. In this way the elastic valve flap 3 can be inserted into the annular body by pressing it from a position oriented beyond the closed position, onto the abutment ledge 7 into the closed position from which, during operation, it is unable to be removed by hydrodynamic forces.

In order for the attachments 4 of the valve flap 3 to be able to enter the concave recesses 5 and 6 without significant deformation of the annular body 1, recesses 8 and 9 are provided which communicate with the recesses 5 and 6 to form a passage for the convex portions 4 toward the edge of the annular body. These supplemental recesses 8 and 9 may be provided by a milling tool having the dimensions of the convex portions 4. If the annular body 1 were made of plastic material and the valve flap including its attachments 4 were rigid, the attachments would shape themselves into the material in a corresponding manner.

The recesses 8 and 9 preferably end in the region of enlargements (humps) 10 and 11 of the annular body 1 so as to enlarge, in the region of the spherical attachments 4, the axial length of the annular body 1 for accommodating the concave, dome-shaped recesses 5 and 6. In the region of the humps 10 and 11, stops 12 and 13 are provided which bound recesses receiving the disc-shaped portion of the valve flap 3 in the open state (FIG. 3b). The stops 12, 13 ensure that the valve flap is unable to move beyond the vertical position. The stops 12 and 13 and their corresponding recesses have a shape which corresponds to the shape which would be formed by the valve flap being turned about 90° in the plastic annular body 1 from the closed position into the open position, with the larger diameter remote from the axis of rotation displacing the material of the annular body 1.

The edges which bound the recesses 8 and 9 and which are visible on the other side of the stops 12 and 13 in the plan view of FIG. 1, have an outwardly oriented slope so that, in the plan view, the stops 12, 13 together with the adjacent edges, are barb-shaped. Thus, upon insertion of the valve flap when in an open position, the edges of the valve flap slide over the edges adjoining externally the abutment faces 12 and 13 and come to rest in the region of the abutment faces 10 and 11. In this way, the valve flap can be inserted into the annular body without significantly deforming the latter, and by virtue of the effect of the abutment faces 12 and 13, the valve flap, when in an open state, can no longer assume the position in which it was inserted. Insertion may also occur without deformation of the annular body, in which case the valve flap must merely be slightly bent so as to overcome the detent effect of the abutment faces 11 and 12. Since the deformation is able to take place uniformly over the entire diameter of the cardiac valve; no major local material stresses occur.

Figure 3A:
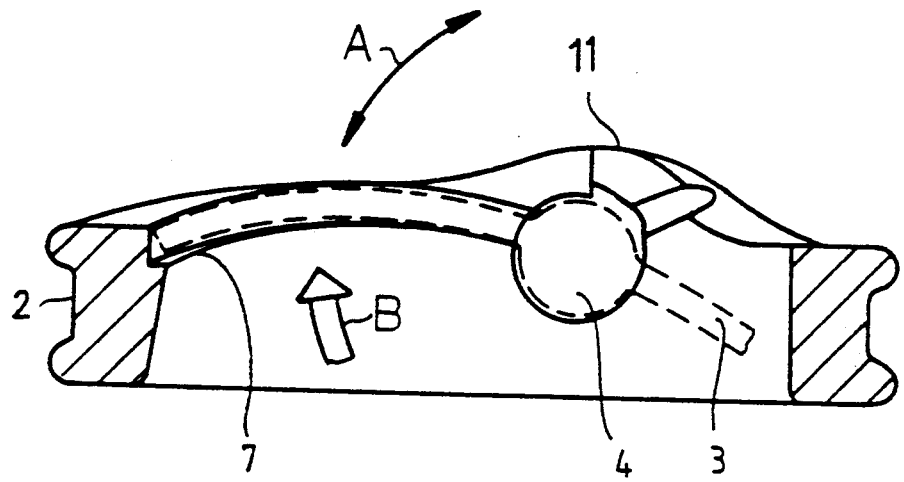
FIGS. 3a and 3b are sectional views along the line III—III of FIG. 1, showing the valve body in two different positions.
Figure 3B:
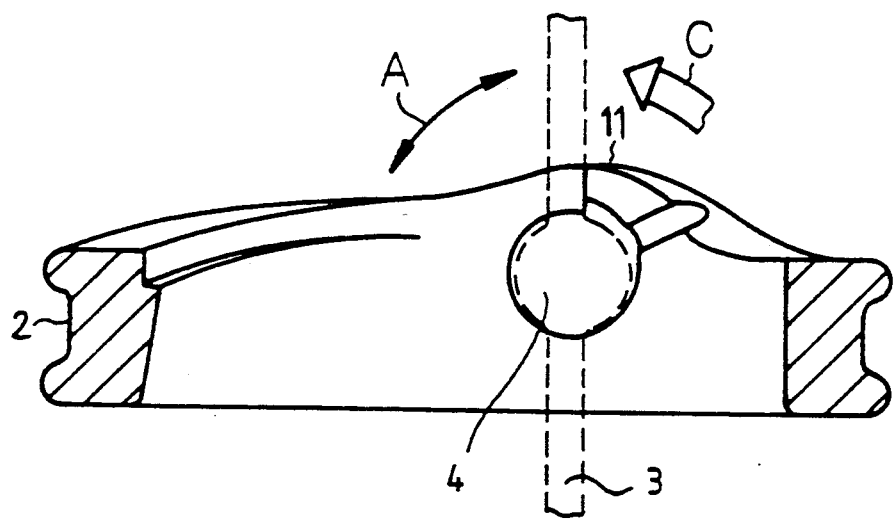

In FIGS. 3a and 3b, the region in which the valve flap 3 is able to freely pivot is shown by arrow A and the movement required to pivot it during insertion is shown by arrows B (FIG. 3a) and C (FIG. 3b).

Figure 4:
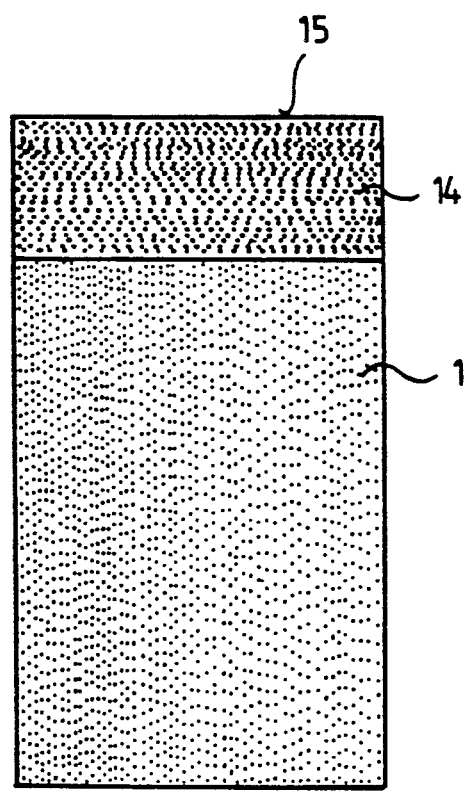
FIG. 4 is a magnified sectional view of a surface portion of the embodiment of FIG. 1.

FIG. 4 shows the surface layer structure of the annular body 1 according to a further feature of the invention. On the surface of the annular body 1, there is provided a pore-free coating 14 of amorphous silicon oxide or pyrolytic or amorphous silicon carbide (a-SiC:H) as a semiconductive material, formed as a precipitation product of a mixture including silane ($SiH_4$) and/or methane ($CH_4$) and whose surface 15 has an antithrombogenic configuration.

The coating 14 has a maximum thickness of between less than 1 $\mu$m and 10 $\mu$m and has a comparatively high modulus of elasticity as well as a relatively smaller elastic range. The surface 15 has a peak-to-valley height (roughness) of about 0.1 $\mu$m or less. The state density of the coating 14 lies in the region of the energy level of the protein states in blood, that is, at $10^{18} cm^{-3} eV^-$, or less. The configuration of the surface 15 prevents direct charge exchanges between coagulation-specific proteins and the implant surface.

In a further embodiment, the semiconductive layer 14 is a microcrystalline material, particularly amorphous silicon-nitride (a-SiN:H). The surface 15 of this embodiment has characteristics corresponding to the embodiment described above.

It will be understood that the above description of the present invention is susceptible to various modifications, changes and adaptations, and the same are intended to be comprehended within the meaning and range of equivalents of the appended claims.

What is claimed is:

1. A cardiac valve prosthesis comprising:
   a rotatably mounted, disc-shaped valve flap, said flap including two outwardly oriented convex attachments which face opposite directions from one another at points of intersection of a secant of said valve flap with an edge of said valve flap, said flap being pivotable about said secant; and
   an annular body including an interior wall having first recesses for receiving said convex attachments and for providing a bearing for said valve flap, said interior wall having means for facilitating insertion of said valve flap into said first recesses including second recesses communicating with said first recesses to form a passage for the convex attachments during insertion of the valve flap when the valve flap is in an orientation which is beyond a fully open or a fully closed position thereof; said second recesses extending from said first recesses toward an exterior edge of said annular body; said annular body further including first and second stops for determining an open and a closed position for said valve flap, wherein at least one of said first and second steps has a barb-shaped cross section.

2. The cardiac valve prosthesis according to claim 1, wherein, in the open position of the valve flap, said first stop is disposed downstream from said bearing, as viewed in the direction of blood flow through the valve prosthesis.

3. The cardiac valve prosthesis according to claim 1, wherein said second stop comprises an edge disposed at said interior wall of said annular body.

4. The cardiac valve prosthesis according to claim 1, wherein said second recesses are dimensioned so that the passage they form with said first recesses accommodates said valve flap during insertion without substantially deforming said annular body.

5. The cardiac valve prosthesis according to claim 1, wherein said second stop comprises a ledge extending within said annular body tangentially along said interior wall in a region between said first recesses, said ledge preventing movement of said valve flap in a direction beyond the closed position.

6. The cardiac valve prosthesis according to claim 1, wherein said annular body has a surface having a coating of a semiconductor material disposed thereon, said semiconductive material being amorphous and wherein said coating has a thickness in a range from less than 1 $\mu$m to about 10 $\mu$m and a roughness of about 0.1 $\mu$m.

7. The cardiac valve prosthesis according to claim 1, wherein said annular body has a surface having a coating of a semiconductive material dispose thereon, said semiconductive material being amorphous and wherein the state density of said coating at the energy level of protein states in blood is sufficiently low to prevent a charge exchange between coagulation-specific proteins and said surface.

8. The cardiac valve prosthesis according to claim 1, wherein said annular body has a surface having a coating of a semiconductive material disposed thereon, said semiconductive material being amorphous, said coating comprising one of pyrolytic and amorphous silicon carbide (a-SiC:H), amorphous silicon nitride and amorphous silicon oxide.

9. The cardiac valve prosthesis according to claim 1, wherein said annular body has a surface having a coating of a semiconductive material disposed thereon, said semiconductive material being amorphous, said coating comprising one of pyrolytic and amorphous silicon carbide (a-SiC:H), and wherein said semiconductive material is microcrystalline.

* * * * *